United States Patent [19]

Westerhoff

[11] 4,157,715

[45] Jun. 12, 1979

[54] INTRACORPORAL DRIVE TO PRODUCE A CONTINUOUS TRACTION OR PRESSURE AND METHOD OF OPERATING THE SAME

[76] Inventor: Erhard Westerhoff, Littenweiler Strasse 23, 7800 Freiburg, Fed. Rep. of Germany

[21] Appl. No.: 886,074

[22] Filed: Mar. 13, 1978

[30] Foreign Application Priority Data

Mar. 25, 1977 [DE] Fed. Rep. of Germany ....... 2713837

[51] Int. Cl.² .................. A61F 5/04; A61B 17/18
[52] U.S. Cl. .................. 128/92 D; 128/84 R; 128/92 G
[58] Field of Search ............... 128/84 R, 84 B, 84 C, 128/83, 92 R, 92 B, 92 BC, 92 D, 92 G

[56] References Cited

U.S. PATENT DOCUMENTS

| 3,900,025 | 8/1975 | Barnes, Jr. .................. 128/92 D |
| 3,976,060 | 8/1976 | Hildebrandt et al. ........... 128/84 R |
| 4,096,857 | 6/1978 | Cramer et al. ................ 128/84 R |

FOREIGN PATENT DOCUMENTS 1239266  7/1960  France .................. 128/92 D

Primary Examiner—Ronald L. Frinks
Attorney, Agent, or Firm—Werner W. Kleeman

[57] ABSTRACT

An intracorporal drive, and method of operating the same, especially for an extension unit for extension osteotomy and for a compression unit for pressure osteosynthesis, wherein the driving power is generated by the osmotic pressure between two differently concentrated solutions separated from each other by a semipermeable diaphragm or membrane. The solution of low concentration also can be substituted by pure solvent.

15 Claims, 2 Drawing Figures

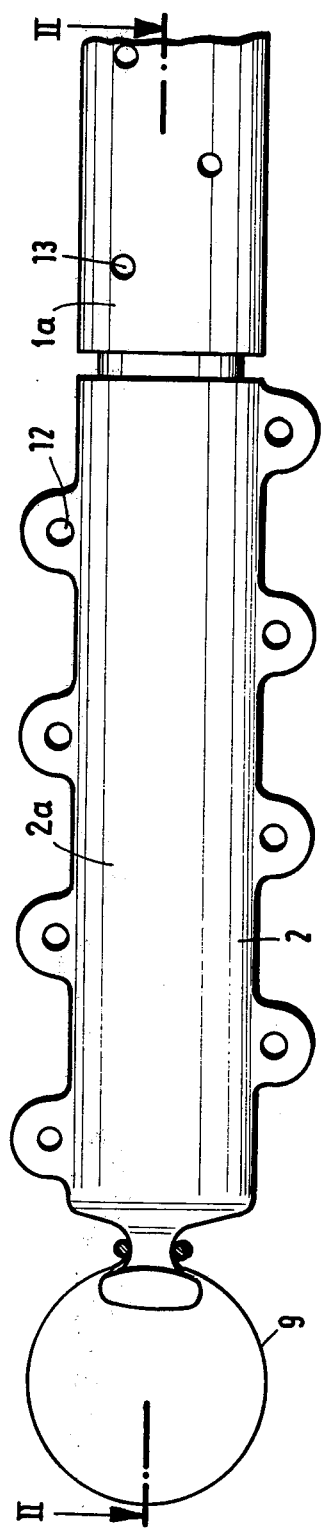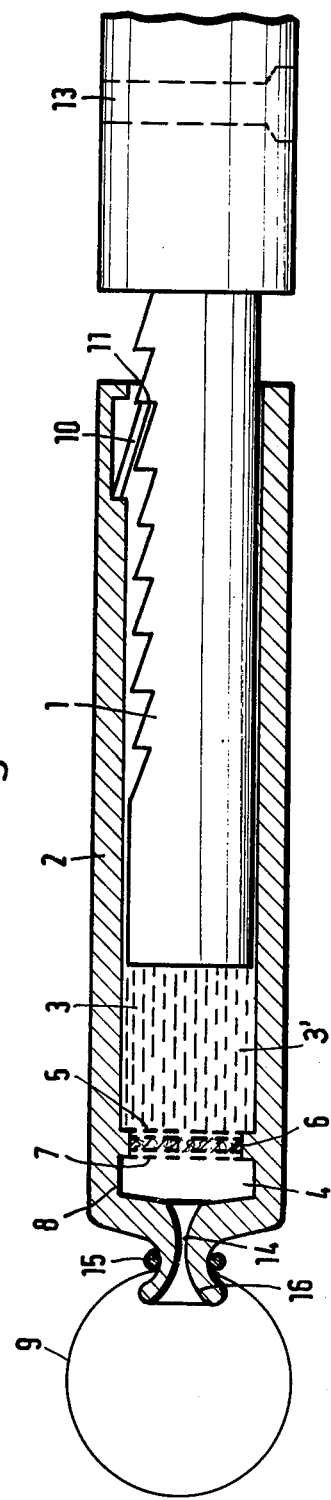

INTRACORPORAL DRIVE TO PRODUCE A CONTINUOUS TRACTION OR PRESSURE AND METHOD OF OPERATING THE SAME

BACKGROUND OF THE INVENTION

The present invention concerns an intracorporal drive for producing a continuous traction or pressure, respectively, especially for an extension unit intended for extension osteotomy or for a compression unit intended for pressure osteosynthesis, and to method of operation thereof.

Drives, for instance for an extension unit for extension osteotomy comprising two telescopically adjustable parts which, after having cut the bone, are both separately screwable to the bone to be extended and which are prevented from backward movement, are known in various constructions. German Pat. No. 2,417,233 discloses, for example, a motor drive disposed in the extension unit which is controlled by electrotechnical means. Such a drive is comparatively expensive and requires a highly specified outer covering in order to prevent any contact with the surrounding tissue. The use of a pressure gas drive, which is also described in the above mentioned German patent publication, is rather problematic, because a strong intracorporal pressure wave could be produced in case of breakage of the extension unit.

SUMMARY OF THE INVENTION

Hence, it is a primary object of the present invention to provide a drive which can be manufactured without great technical resources and which as far as possible is sealed against the surrounding tissue after implantation.

Another object of the invention is to provide a new and improved construction of drive which does not require any control mechanism after the implantation of the unit with which it is equipped.

Still a further object of the present invention concerns a novel method of operating an intracorporal drive.

According to the invention, these objects and others are fulfilled by the use of the osmotic pressure between a first solution of higher concentration and a second solution of lower concentration or a pure solvent, respectively, which solutions are separated by a semipermeable membrane or diaphragm, whereby means are provided to keep the solution of lower concentration or the pure solvent, as the case may be, in contact with the semipermeable diaphragm.

The choice of the semipermeable diaphragm depends upon the type of solutions to be separated. Principally, all types of diaphragms or membranes known for technical applications—e.g. for the reverse osmosis—can be used as far as they are toxicologically sufficiently defined and unobjectionable. Since direct contact with the organism is extensively excluded, the safeness must above all be proven by migration tests (i.e. tests about the migration of additives, as e.g. plasticizers, from the diaphragm into a solvent). As examples may be named: diaphragms based on cellulose acetate, especially cellulose acetate itself, cellulose acetate octanoate or cellulose acetate palmitate as well as diaphragms based on polyamides or cellulose polymerisates.

As solvents there can be used low-molecular or high-molecular substances which are toxicologically unobjectionable and which are, if possible, also found physiologically in the organism. This would, for example, be the case for aqueous solutions of common salt and various sugars. Since these substances can be absorbed by the body in low concentration without any harm, and since they are already contained in the blood serum, it is advantageous, especially in order to prevent any bodily harm, to use as the solution of lower concentration, i.e. as the component of the drive which delivers solvent, a physiological common salt solution, i.e. a 0.9% aqueous solution or a solution of 30 mg glucose in 100 ml water.

One of the advantages of the present invention is that because of the use of the osmotic pressure as driving means it is possible to dispense with a complicated design of the units and controls and to determine the desired extension by means of a previous determination of the amount of concentrated solution and solvent.

The magnitudes of the theoretically possible pressures and distances are given in the following calculations of the osmotic pressure of concentrated aqueous common salt solutions. The following figures related to a cross-sectional area of 1 $cm^2$ with pure $H_2O$ as the substance delivering solvent, are obtained for a body temperature of 37° C. and ideal solutions, i.e. without taking into account molecular forces or frictional forces, and so forth.

| Concentration Mol NaCl/Liter $H_2O$ | Amount $H_2O$ $cm^3$ | Osmotic pressure/bar | Distance cm |
|---|---|---|---|
| 5.7 (approx. 330 g/l) | approx. 15 | approx. 250 | approx. 16 |
| 4.275 (approx. 250 g/l) | approx. 20 | approx. 195 | approx. 22 |
| 3.42 (approx. 195 g/l) | approx. 25 | approx. 161 | approx. 27 |

It is understood for anybody skilled in the art that these values cannot be reached in practice. Due to the existing losses, the pressures and distances are considerably—at least approximately one-third—lower. It is therefore advisable to determine these values empirically for each individual case.

Furthermore, it should be mentioned that on the side of high concentration, the substance of the solution does not necessarily need to be dissolved completely. Functioning of the new drive of this development is also possible if, instead of a highly concentrated solution, there is used a saturated solution from which the substance of the solution has partly precipitated.

Moreover, the principle of making use of the osmotic pressure intracorporally can be used for various other applications in medicine and is not limited to the examples mentioned herein.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 shows a top view of an extension unit for the extension osteotomy equipped with the drive according to the invention; and FIG. 2 shows a section through the unit according to FIG. 1, taken substantially along the line II—II thereof.

DETAILED DESCRIPTION OF THE PREFERRED EMBODIMENTS

Describing now the drawings, the extension unit to be driven consists of two parts 1a and 2a which are each separately fastened to the bone to be extended by means of the holes or bores 12 and 13, respectively and not particularly shown threaded bolts or other appropriate fastening expedients. The two parts 1a and 2a are telescopically adjustable after having cut the bone. The parts 1a and 2a of the unit form a piston-cylinder unit 1, 2. A backward or return movement between the piston 1 and the cylinder 2 is prevented by a well known and therefore not further described backward or return motion stop 10, 11. Between the piston 1 and the cylinder 2, there is provided a conventional sealing element, for example an O-ring, which is not shown in the drawing, made of elastic material which seals the cylinder chamber or compartment against its surroundings. The osmotic pressure generated in a concentrated solution 3' by a solvent 4 penetrating through a semipermeable diaphragm 5 is used as the drive for a relative displacement between the piston 1 and the receiving cylinder 2.

The semipermeable diaphragm or membrane 5, fabricated for instance of cellulose acetate, bears against a porous layer 6 which, in turn, is mechanically retained by a perforated bracket or support plate 7.

The diaphragm 5 separates the inner space or chamber 3 of cylinder 2 which contains the solution 3' from another chamber or cavity 8 integrated in cylinder 2. The chamber 8 is provided with a channel 14 which flow communicates with a prestressed elastic container 9 defining a chamber. The container 9 is connected by means of a clamp element 15 to inlet 16 of the chamber 8 which extends outwardly to form such channel 14.

The chamber 8 and container 9 are filled with a low concentration solution or a pure solvent. The prestressing of container 9, which also can be accomplished, instead of by the rubber-like elastic wall, for instance by means of a spring-loaded piston, ensures that diaphragm 5 is continuously moistened or imbued by the low concentrated solution or the pure solvent, as the case may be, at least during the intended duration of effect of the drive.

As already mentioned, the volumes of the chambers 8 and 9 can be used to control the distance covered by piston 1 because of the osmotic pressure and/or the duration of effect of the drive; since as soon as, due to the increasing equalization of the concentration, the osmotic pressure no longer can overcome the counteracting forces, the drive comes to standstill. This point in time is determined by the initial dilution and the amount of solvent in chambers 8 and 9.

The intensity of the initial osmotic pressure can be influenced, among other things, by the difference of the concentration in the chambers 3 and 8 and by the thickness of the diaphragm 5, whereas the feed or advance speed of piston 1 can be altered to a certain degree by varying the area or size of diaphragm 5 which is available for the penetration of the solvent, also by the thickness and/or type of diaphragm, or combinations of the foregoing factors.

Instead of using a piston mechanism to produce the feed movement, it would be conceivable to possibly use another system, for instance an elastic system while utilizing the elongation of a housing wall for the solution in chamber 3, such as by structuring the cylinder wall to be expansible or elongatable.

In the present example under discussion, there is used an aqueous solution saturated to the solubility limit with common salt as the concentrated solution in chamber 3. This solution can be easily obtained from a solution saturated at 25° C.—or another temperature below the normal body temperature—from which the liquid phase is removed. For the increased body temperature of approximately 37° C. there is then obtained an almost saturated solution.

In the same way, there can be produced other examples for a concentrated solution, e.g. a glucose or grape sugar solution which likewise is also almost saturated.

Since pure water has a toxic effect in the body, it is advantageous to use as solutions releasing solvent in the chambers 8 and 9 diluted solutions of the same substances. Advantageously, these diluted solutions are used in a manner such that they do not differ too much from the concentration of a physiological common salt solution (0.9%) or a blood sugar level (60 mg/100 ml), respectively, at the end of the effectiveness of the drive.

It is to be understood that all solutions used sterilized before they are filled into the drive.

While there are shown and described present preferred embodiments of the invention, it is to be distinctly understood that the invention is not limited thereto, but may be otherwise variously embodied and practiced within the scope of the following claims.

ACCORDINGLY,

What I claim is:

1. An intracorporal drive for selectively producing a continuous traction or pressure, especially for an extension unit intended for extension osteotomy or for a compression unit intended for pressure osteosynthesis, comprising:

means defining a first chamber and a second chamber;

a semipermeable diaphragm separating said first and second chambers from one another;

said first chamber being capable of being filled with a first solution of higher concentration;

said second chamber being capable of being filled with a second solution of lower concentration or a pure solvent;

means for maintaining the solution of lower concentration or the pure solvent in contact with the semipermeable diaphragm;

said semipermeable diaphragm separating the first solution of higher concentration and the second solution of lower concentration or the pure solvent from one another, there being utilized as the drive force for the drive the osmotic pressure between the first solution of higher concentration and the second solution of lower concentration or the pure solvent.

2. The intracorporal drive as defined in claim 1, wherein:

said means defining said first chamber and said second chamber comprises a pair of interfitting coacting parts movable relative to one another.

3. The intracorporal drive as defined in claim 2, wherein:

said pair of relatively movable parts comprise a piston-and-cylinder unit.

4. The intracorporal drive as defined in claim 1, wherein:

said maintaining means comprises a prestressed elastic container housing at least part of the solution of lower concentration or the pure solvent.

5. The intracorporal drive as defined in claim 1, further including:

a porous layer against which bears said semi-permeable diaphragm; and a perforated support plate for supporting said porous layer.

6. The intracorporal drive as defined in claim 1, wherein:

said means defining said first and second chambers comprises a pair of interfitting telescopic parts defining a piston-and-cylinder unit;

said first chamber being disposed adjacent said piston;

said osmotic pressure increasing the volume of the first chamber containing the first solution of higher concentration, and which increased volume of said first chamber is converted by means of said piston into a feed movement.

7. The intracorporal drive as defined in claim 1, wherein:

said means defining said first chamber and said second chamber incorporates structure cooperating with said first chamber such that an increase in the volume of the first chamber containing the first solution of higher concentration brought about by the osmotic pressure is converted by means of said structure into a feeding movement.

8. The intracorporal drive as defined in claim 6, wherein:

the displacement path covered by said piston is controlled by the employed amount of second solution of lower concentration or pure solvent.

9. The intracorporal drive as defined in claim 6, wherein:

the speed of feeding movement of the piston is selectively controlled by any one of (1) the size of the surface of the diaphragm, (2) the thickness of the diaphragm, (3) the type of diaphragm used, or combinations thereof.

10. The intracorporal drive as defined in claim 6, further including:

stop means for preventing reverse movement opposite to said feeding movement between the piston and cylinder.

11. A method of operating an intracorporal drive for selectively producing a continuous traction or pressure, comprising the steps of:

providing a first chamber and a second chamber;

separating said first and second chambers from one another by means of a semipermeable diaphragm;

filling said first chamber with a first solution of higher concentration;

filling said second chamber with a second solution of lower concentration or a pure solvent;

maintaining the solution of lower concentration or the pure solvent in contact with the semipermeable diaphragm;

diffusing by osmosis the second solution of lower concentration of the pure solvent through the semipermeable diaphragm into said second chamber containing said first solution of higher concentration; and utilizing the resultant osmotic pressure as the drive force for the intracorporal drive.

12. The method as defined in claim 11, further including the steps of:

controlling the intensity of the drive force by controlling the employed amount of the second solution of lower concentration or the pure solvent.

13. The method as defined in claim 11, further including the steps of:

converting an increase in volume of the first chamber containing the first solution of higher concentration into feeding movement of a piston.

14. The method as defined in claim 13, further including the steps of:

controlling the speed of the feeding movement of the piston by at least any one of (1) the size of the surface of the diaphragm, (2) the thickness of the diaphragm, (3) the type of diaphragm employed, or combinations thereof.

15. The method as defined in claim 13, further including the steps of:

retarding reverse movement of said piston in a direction opposite to said feeding movement.

* * * * *